United States Patent [19]

Shochat et al.

[11] Patent Number: 5,514,363

[45] Date of Patent: *May 7, 1996

[54] METHOD FOR RADIOLABELING ANTIBODY FRAGMENTS

[75] Inventors: Dan Shochat, Maplewood; Hans J. Hansen, Westfield; Robert S. Wu, West Orange, all of N.J.

[73] Assignee: Immunomedics, Inc., Morris Plains, N.J.

[*] Notice: The term of this patent shall not extend beyond the expiration date of Pat. No. 5,328,679.

[21] Appl. No.: 1,419

[22] Filed: Jan. 7, 1993

Related U.S. Application Data

[63] Continuation of Ser. No. 581,913, Sep. 13, 1990, abandoned, which is a continuation of Ser. No. 176,421, Apr. 1, 1988, Pat. No. 5,061,641.

[51] Int. Cl.[6] .................................................. A61K 39/395
[52] U.S. Cl. .................... 424/1.49; 424/1.69; 530/391.3; 530/391.5
[58] Field of Search ..................... 424/1.1, 1.49, 424/1.69; 435/544, 545, 804; 530/406, 408, 412, 417, 387.1, 391.1, 391.3, 391.5, 402, 403, 404

[56] References Cited

U.S. PATENT DOCUMENTS

| | | | |
|---|---|---|---|
| 4,652,440 | 3/1987 | Paik et al. | 424/1.1 |
| 4,877,868 | 10/1989 | Reno et al. | 436/547 |
| 5,053,493 | 10/1991 | Pak et al. | 530/402 |
| 5,061,641 | 10/1991 | Shochat et al. | 530/402 |
| 5,078,985 | 1/1992 | Rhodes | 424/1.1 |
| 5,102,990 | 7/1992 | Rhodes . | |
| 5,128,119 | 7/1992 | Griffiths et al. . | |
| 5,328,679 | 7/1994 | Hansen et al. . | |

FOREIGN PATENT DOCUMENTS

| | | |
|---|---|---|
| 0237150 | 9/1987 | European Pat. Off. . |
| WO88/07382 | 10/1988 | WIPO . |

OTHER PUBLICATIONS

Nuclear Medicine, 21:59–62, (1980).
Pettit et al (1980) Cancer Res. 40:3043–3045.
Pettit et al, "Improved Protein Labeling by Stannous Tartrate Reduction of Pertechnetate," *The Journal of Nuclear Medicine*, 21:59–62, (1980).

Primary Examiner—Margaret Parr
Assistant Examiner—Phillip Gambel
Attorney, Agent, or Firm—Foley & Lardner

[57] ABSTRACT

A protein containing at least one pendant sulfhydryl group is directly radiolabeled with a radiometal which binds tightly to sulfhydryl groups, using one or more pendant sulfhydryl groups on the protein as endogenous ligands and optionally using an exogenous ligand which binds tightly to the radiometal ion to further stabilize the chelate.

20 Claims, No Drawings

METHOD FOR RADIOLABELING ANTIBODY FRAGMENTS

This application is a continuation of application Ser. No. 07/581,913, filed Sep. 13, 1990, now abandoned, which in turn is a continuation of Ser. No. 07/176,421, filed Apr. 1, 1988, now U.S. Pat. No. 5,061,641, issued Oct. 29, 1991.

BACKGROUND OF THE INVENTION

The present invention relates to a method and kit for direct radiolabeling of a protein with a radiometal ion of a radionuclide that binds tightly to sulfhydryl groups, using one or more pendant sulfhydryl groups as endogenous ligands and optionally using an exogenous ligand which binds tightly to the radiometal ion to further stabilize the chelate.

It is known that certain radiometals bind tightly to sulfur ligands, including, e.g., Tc-99m from reduced pertechnetate, Re-186 and Re-188 ions, Cu-67 ions, Hg-197 ions and Bi-212 ions. Some of these radiometals have been bound to proteins, especially antibodies or antibody fragments, using conjugated chelating groups such as diethylenetriaminepentaacetic acid (DTPA) or a variety of sulfur/nitrogen ($S_2N_2$) chelators such as bis-thiosemicarbazones and the like.

Methods have been reported for binding Tc-99m ions directly to antibodies by pre-tinning the protein and then contacting the resultant material with pertechnetate. This procedure often does not work well and some of the radiometal is bound to sites which are comparatively labile in the presence of blood and other bodily fluids or tissues. The mechanism of the pre-tinning process is not well understood and the reasons for production of labile sites of labeling have not been elucidated.

It is also known that proteins containing disulfide bonds can be reduced to produce pendant sulfhydryl groups. If the disulfide bonds link polypeptide chains which are not themselves joined, e.g., antibody light/heavy chains, reductive cleavage thereof can dissociate the protein into smaller fragments. An example of this is the reductive cleavage of antibody F(ab')$_2$ fragments to form Fab' fragments using disulfide reducing agents such as cysteine, dithiothreitol, mercaptoethanol and the like.

Direct labeling of a protein has the advantage that chelate conjugates are obviated. However, attempts to use such radiolabeled proteins for in vivo applications, e.g., antibody-targeted tumor imaging and therapy, has revealed problems due to loss of the label to other organs which retain it and cause both high background for certain types of imaging and slow clearance of the label from organs such as the liver, spleen and kidneys. The latter problem can in turn cause hepatic and/or renal crisis for the therapy patient due to severe compromise of the affected organ by the high levels of radiation.

A need continues to exist for a direct method for radiolabeling a protein that produces a good yield of a stable radiolabeled product which retains the label in the presence of blood and other body fluids and tissues.

OBJECTS OF THE INVENTION

Accordingly, one object of the present invention is to provide a method for direct radiolabeling of a protein with a radiometal which does not require conjugation to the protein of a chelator for ions of the radionuclide.

Another object of the invention is to provide a method of further stabilizing sulfhydryl-bound radiometal ions on a protein.

A further object of the invention is to provide a method for radio-labeling a protein which produces high yields of labeled product with minimal contamination with by-products.

Yet another object of the invention is to provide a convenient and efficient radiolabeling method and kit for use in introducing Tc-99m into an antibody or antibody fragment.

Upon further study of the specification and appended claims, further objects and advantages of this invention will become apparent to those skilled in the art.

SUMMARY OF THE INVENTION

The foregoing objects are achieved by providing a method for radio-labeling a protein, comprising the step of contacting a solution of a protein containing at least one pendant sulfhydryl group with a solution of radiometal ions of a radionuclide which tightly binds to sulfhydryl groups, and recovering the resultant solution of radio-labeled protein.

Preferred embodiments include applying the method of the invention to produce radio-labeled antibodies or antibody fragments, especially Fab and Fab' fragments. The method of the invention is advantageously applied to label proteins, especially antibody fragments, with Tc-99m in a procedure which is simple and practical for the nuclear medicine physician.

The invention also provides radio-labeled proteins and kits for effecting the labeling process of the invention, especially Tc-99m-labeled antibodies and antibody fragments and kits for their preparation.

DETAILED DESCRIPTION

The present inventors have found that a protein, e.g., an antibody or antibody fragment, having free pendant sulfhydryl groups can selectively bind radiometal ions to form tight bonds to the sulfhydryl groups that are quite stable in blood and other bodily fluids and tissues. Attempts to repeat pretinning procedures of others with F(ab')$_2$ antibody fragments were unsuccessful in achieving Tc-99m labeling. Further investigation revealed that failure to incorporate the Tc-99m label correlated with absence of monovalent fragments containing free sulfhydryl groups in the pre-tinned material. Reduction of the F(ab')$_2$ fragment with cysteine, followed by separation of the excess reducing agent on a short sizing gel column, and addition of the resultant Fab'-SH fragment to reduced pertechnetate resulted in binding of all of the reduced pertechnetate to the Fab'-SH.

The cleaved F(ab')$_2$ fragment containing at least one free sulfhydryl group will be termed "Fab'-SH" herein. Cleaved F(ab)$_2$ will be termed "Fab-SH", cleaved whole immunoglobulin containing at least one free sulfhydryl group will be termed "Fabc'-SH" and will denote complete cleavage of the disulfide bonds linking the heavy chains of the antibody, with concomitant production of sulfhydryl groups and separation of the two halves of the "Y-shaped" molecule into two light-heavy chain fragments. Incomplete reduction of whole immunoglobulin or fragment, with production of fewer free sulfhydryl groups than the number of disulfide bonds linking the heavy chains, or introduction of sulfhydryl groups into a protein, will be denoted by appending "-SH" to the abbreviation for the partially cleaved or derivatized species. Thus, e.g., partially reduced IgG which has fewer free sulfhydryl groups than the intact IgG will be denoted "IgG-SH". The most general case of a protein with one or more pendant sulfhydryl groups will be denoted Prot-SH.

The labeling method and kit of the invention may be used to bind radiometals to any protein. Those proteins which contain sulfhydryl groups can be labeled directly. Those which contain disulfide groups, normally linked through a cystine residue, can be treated with a reducing agent to generate sulfhydryl groups. This may result in fragmentation of the protein if the disulfide bond links polypeptide chains which are not continuous, or it may merely result in chain separation, possibly involving a change in conformation of the protein if the disulfide bond joins remote segments of a single polypeptide chain. Sulfhydryl groups can be introduced into a polypeptide chain by conventional methods, e.g., use of Traut's Reagent, i.e., iminothiolane, using conventional conditions, e.g., those disclosed in Blattler et al., Biochem., 24:1517–1524, 1985.

The method of the invention is attractive for labeling antibodies and antibody fragments, although proteins such as albumin, enzymes, hormones, immune modulators and the like can also be labeled. Antibodies contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

It will also be understood that the antibodies or antibody fragments to be radiolabeled can be antibodies which bind to antigens which include but are not limited to antigens produced by or associated with tumors, infectious lesions, myocardial infarctions, atherosclerotic plaque, or normal organs or tissues.

The present method is particularly well suited to radiolabeling sulfhydryl-containing monovalent antibody fragments, e.g., Fab-SH or Fab'-SH, since they can be generated by reductive cleavage of divalent $F(ab)_2$ or $F(ab')_2$ fragments with an appropriate conventional disulfide reducing agent, e.g., cysteine, dithiothreitol, 2-mercaptoethanol, dithionite or the like. Reduction is preferably effected at pH 5.5–9.5, preferably 6.0–6.8, more preferably 6.1–6.4, e.g., in citrate, acetate or phosphate buffer, and advantageously under an inert gas atmosphere. Reduction is faster at higher pH, but reoxidation is also faster, and the optimal pH will be one where reduction is reasonably rapid, but reoxidation, including formation of mixed disulfides with thiol reducing agents, is negligible. Care must also be taken to avoid overly powerful reducing agents that will reduce light/heavy chain disulfide bonds in competition with heavy/heavy chain disulfide bonds in immunoglobulin proteins. Cysteine is preferred for such disulfide reductions and other thiols with similar oxidation potentials to cysteine will also be advantageously used. The ratio of disulfide reducing agent to protein is a function of interchain disulfide bond stabilities and must be optimized for each individual case. Cleavage of $F(ab')_2$ antibody fragments is advantageously effected with 10–20 mM cysteine and a protein concentration of about 10 mg/ml.

The Fab-SH or Fab'-SH fragments can be generated in situ and the resultant solution used directly, but preferably the fragments are then passed through a short sizing gel column which will trap low molecular weight species. Suitable such sizing gel columns include, e.g., dextrans such as Sephadex G-25, G-50 (Pharmacia),; Fractogel TSK HW55 (EM Science), polyacrylamides such as P-4, P-6 (BioRad), and the like.

Cleavage can be monitored by, e.g., size exclusion HPLC, to adjust conditions so that Fab or Fab' fragments are produced to an optimum extent, while minimizing light-heavy chain cleavage, which is generally less susceptible to disulfide cleavage. The eluate from the sizing gel column is then passed into a solution of the radiometal ions to be used for labeling. Alternatively, the Fab-SH or Fab'-SH can be kept at low temperature, e.g., in the refrigerator, for several days to several weeks, preferably at a pH of 3.5–5.5, more preferably at pH 4.5–5.0, advantageously under an inert gas atmosphere, e.g., nitrogen or argon.

It is convenient to lyophilize the Fab-SH or Fab'-SH for ease of storage and stabilization. This is advantageously effected at pH of about 5.5, from a solution of a volatile buffer, e.g., ammonium acetate, and preferably also in the presence of a stabilizer to prevent aggregation, e.g., a sugar such as trehalose or sucrose. Such lyophilization conditions are conventional and well known to the ordinary skilled artisan. The solution of antibody fragment also can be frozen and then thawed prior to use, but this carries greater risk of reoxidation and aggregation of the protein.

In situ generation of sulfhydryl groups, e.g., by cleavage of divalent fragments to their monovalent components, and separation of the resultant thiol-containing proteins also can be effected using a spin column. Spin columns are preferably short gel-packed columns, which can be in the form of a syringe, fitted with a needle adapter which can be used to direct the column effluent through a needle into a container for a subsequent step. Centrifugation of the spin column results in expression of the void volume.

Sizing gel columns that can be used in a spin column technique include, e.g., dextrans such as Sephadex G-25, G-50 (Pharmacia),; Fractogel TSK HW55 (EM Science), polyacrylamides such as P-4, P-6 (BioRad), and the like.

The gel in the spin column is advantageously pre-equilibrated with the same buffer used for the labeling reaction, preferably also containing a stabilizer such as ascorbate for the thiol groups. A solution of sulfhydryl-containing protein, e.g., Fab'-SH which, in a preferred embodiment is prepared in situ by reacting $F(ab')_2$ with cysteine, is loaded onto the column. Then the column is centrifuged, with the outlet, e.g., a syringe needle, extending into a vial containing a solution of radiometal ions, e.g., reduced pertechnetate or perrhenate, cupric ions, mercuric ions, lead/bismuth ions or the like. Expression of the void volume will leave low molecular weight thiol reducing agent in the column while causing the Fab'-SH to pass into the vial and take up the radiometal ions.

Radiometals which can be bound to proteins using the present method are those which bind tightly to sulfhydryl groups. Generally, these will be metal ions which form relatively insoluble sulfides in the conventional qualitative analysis schemata. These include, but are not limited to, Tc-99m, Re-186, Re-188, Cu-67, Hg-197, Pb-203, Pb/Bi-212 and the like. Radiometals having a gamma emission energy in the range of about 50–500 KeV are useful for scintigraphy. Positron emitters can also be used for imaging applications. Beta and alpha emitters are useful for therapy. Technetium-99m is a preferred radio-label for scintigraphy because of its ready availability and ease of preparation from commercial pertechnetate generators.

Rhenium is found just below technetium in the periodic table, has the same outer shell electronic configuration, and therefore is expected to have very similar chemical properties, especially the behavior of analogous compounds. In fact, rhenium compounds behave similarly to technetium compounds insofar as reduction and chelation are concerned but their greater susceptibility to oxidation requires greater care in handling.

The radioisotope Re-186 is attractive for both imaging and therapy. It has a half-life of about 3.7 days, a high LET beta emission (1.07 MeV) and a convenient gamma emission energy (0.137 MeV). Like technetium, rhenium is produced from perrhenate, and the reduced rhenium ions can bind non-specifically to protein. Accordingly, a method for Re-186 labeling of proteins, wherein the reduced perrhenate is bound to sulfhydryl groups of a protein molecule such as an antibody, would be advantageous. Re-188 is a generator-produced beta and gamma emitter with a half-life of about 17 hours and could be useful for imaging and therapy.

Copper ions are also tightly chelated by sulfur chelators. Cu-67 is another attractive radionuclide for imaging and therapy. It has a half-life of about 2.6 days, a beta emission (0.570 MeV) and a gamma emission (0.185 MeV), although the beta energy is relatively low. Cu-67 is relatively expensive and not readily available at present, although such conditions can change as demand develops. It has the advantage that it forms tight chelates with thiols, the labeling is simple and rapid, and requires no reducing agent for the radiometal.

Other radionuclides with similar chelation behavior to copper, e.g., mercury and lead, also could be bound to thiol-containing compounds according to the method of the invention. Hg-197 has a half-life of about 1.5 days, and emits gamma radiation in an energy range of 78–268(58 KeV, and Pb-203 is a strong gamma-emitter at about 275 KeV, with a half-life of about 51 hr, making them suitable for gamma scintigraphy. Bi-212 is an alpha-emitter with a half-life of about 1 hr and an energy of 6.09 MeV, making it of considerable interest for in vivo therapy. It is produced in situ from a Pb-212 precursor with emission of gamma radiation of 239 KeV, with a half-life of about 10.6 hr. Thus, antibody conjugates for Bi-212 therapy will be Pb-212-labeled conjugates, and the short-hand notation lead/bismuth or Pb/Bi is used herein to indicate this. It will be understood that the invention is not limited to the exemplified radiometal ions, but is generally applicable to ions that bind tightly to sulfhydryl groups.

By "reduced pertechnetate" or "reduced perrhenate" is meant the species of technetium or rhenium ion formed by chemical reduction of pertechnetate or perrhenate and chelated by the thiol group(s). It is generally thought that reduced pertechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states cannot be excluded and are within the scope of the invention. Copper will normally be in the form of Cu(II), although Cu(I) and/or Cu(III) are not excluded. Mercury will normally be in the form of Hg(I) and/or Hg(II). Lead/bismuth will normally be in the form of Pb(II) or Pb(IV).

Technetium labeling of the sulfhydryl-containing protein is generally effected by conventional methods. Pertechnetate is obtained from a commercially available generator, most commonly in the form of $NaTcO_4$, normally in saline solution. Other forms of pertechnetate may be used, with appropriate modification of the procedure, as would be suggested by the supplier of a new form of generator or as would be apparent to the ordinary skilled artisan.

Reduction is effected by any of a variety of conventional reducing agents, preferably stannous ion, generally in aqueous solution. Other suitable reducing agents include, e.g., dithionite, borohydride, ferrous ion and the like. It will be appreciated that stannous ion can be generated in situ from tin metal, e.g., foil, granules, powder, turnings and the like, by contact with aqueous acid, e.g., HCl.

Pertechnetate is generally used at an activity of about 0.2–10 mCi/ml in saline, e.g., 0.9% ("physiological") saline, buffered at a pH of about 3–7, preferably 3.5–5.5, more preferably about 4.5–5.0. Suitable buffers include, e.g., acetate, tartrate, citrate, phosphate and the like.

When stannous ion is used, it is normally added in excess, to assure complete reduction and utilization of the pertechnetate. Thestannousion concentration is generally in the range of $10^{-4}$–$10^{-3}$ N, stannous ion concentration is generally in the and it is usually added in the form of $SnCl_2$/0.1N HCl.

The reduction is normally effected under an inert gas atmosphere, e.g., nitrogen, argon or the like. The reaction temperature is generally maintained at about room temperature, e.g., 18°–°25° C., and the reaction usually requires about 0.5–3 hrs for substantial completion.

It is often advantageous to add a transchelating agent and/or a stabilizing agent for the stannous ion. It is known that ascorbate can improve specific loading of a chelator with reduced pertechnetate and minimize formation of $TcO_2$, when the reducing agent is stannous ion. Other polycarboxylic acids, e.g., tartrate, citrate, phthalate, iminodiacetate, ethylenediaminetetraacetic acid (EDTA), diethylenetriaminepentaacetic acid (DTPA) and the like, can also be used. While the precise role of such agents is not known, it appears that they chelate stannous ion and may prevent adventitious reactions and/or promote reduction by stabilization of stannic ions, and they may also chelate—and thereby stabilize—certain oxidation states of reduced pertechnetate and perrhenate, thereby serving as transchelating agents for the transfer of these technetium and rhenium ions to the presumably more stable chelation with one or more thiol groups and other nearby ligands on the protein. Such agents will be referred to as "transchelators" herein.

The transchelator should form a chelate with the technetium or rhenium ion that readily and rapidly loses the ion to the sulfur atom(s) of the sulfhydryl group(s) and possibly nearby amine and/or carboxyl groups from lysine or aspartate/glutamate residues. Although polycarboxylic acids are mentioned, by way of illustration, any of a variety of anionic and/or hydroxylic oxygen-containing species could serve this function, e.g., salicylates, acetylacetonates, hydroxyacids, catechols, glycols and other polyols, e.g., glucoheptonate, and the like. The molar ratio of transchelator to sulfhydryl-containing protein should be about 100:1–1:1, preferably 50:1–20:1, more preferably about 10:1.

The transchelator can be immobilized on a solid support and used to separate reduced pertechnetate or perrhenate from the remaining components of the reducing system used for their generation, or it can be used to retain a radiometal in a form which will permit rapid transfer to sulfhydryl groups of a protein. The advantage of such an expedient is that substantially only the radiometal ion is transferred to the protein when a solution thereof is contacted with the solid phase bearing the chelated radiometal ions. Physical separation of the solid phase will then leave labeled protein, uncontaminated by other ions or components of the labeling reagent system. Ideally, the resultant labeled protein could be used directly as an injectable.

It may be desirable to remove unreacted radiometal and/or reducing agent from the labeled protein. This can be accomplished by adding scavengers for the ions, e.g., chelators which can be similar to the transchelators An alternative to adding such scavengers is passage of the reduction mixture through a column containing derivatized adsorbants capable of trapping pertechnetate, e.g., gel columns with bound chelators for reduced pertechnetate and/or stannous/stannic ions. For example, a polymer column packing with bound iminodiacetic acid, called "Chelex", is available from Bio-Rad. Other such suitable column packings include polymers or gels modified to contain DTPA, EDTA and the like, a number of which are commercially available. The same solid phase bound ligand can be used for transchelation and scavenging, in appropriate cases.

A scavenger for free sulfhydryl groups can be added to the reaction mixture after binding to the radiometal is substantially complete. Suitable such scavengers include, e.g., maleimide, iodoacetamide, iodoacetic acid and the like. After initial determination of the extent of uptake of radiometal by the thiol-containing compound, an amount of scavenger capable of reacting with substantially all of the remaining sulfhydryl groups is used. The excess of such sulfhydryl group scavengers can be further scavenged, if desired, by e.g., cysteine or similar such thiol compound, to render them more soluble and thus more readily excretable, so that the conjugation reaction mixture can be used directly as an injectable preparation. Alternatively, a further separation of low molecular weight materials can be effected prior to injection of the labeled protein.

Rhenium labeling will be effected in substantially the same manner as technetium labeling, with special care being taken to insure the absence of air or oxygen in the system. Re-186 is produced in the form of sodium perrhenate by use of a generator analogous to currently available technetium generators.

Copper labeling will be effected by reaction of a thiol-containing protein with a solution of copper ions, normally Cu(II) ions, in the form of a convenient salt, e.g., chloride, citrate, tartrate or the like, either as available or by mixing of, e.g., the chloride with, e.g., sodium, potassium or ammonium citrate, tartrate or the like. Cu-67 is currently available as $CuCl_2$ from Oak Ridge National Laboratories, Tennessee, or from Los Alamos National Laboratories, New Mexico.

Other metallic alpha-, beta-, gamma- and/or positron-emitting radionuclides which bind preferentially to sulfhydryl groups, e.g., Hg-197, Pb-203, Pb-212, and which are available as salts, or in forms which can be readily converted to salts, can also be chelated using the chelators of the present invention. They can be used advantageously, as radiolabels for imaging or as radiotherapeutic agents, in the form of antibody/fragment conujugates prepared according to the method of the invention. Chelation to the antibody protein is effected analogously to Cu-67 labeling.

Mercury radioisotopes are normally available as $HgCl_2$ or as $Hg(NO_3)_2$, e.g., from Oak Ridge National Laboratories.

Lead/bismuth radioisotopes are normally available from Argonne National Laboratories in the form of a supported radon generator.

An important embodiment of the present invention involves the further stabilization or "capping" of a thiol-bound radiometal ion with one or more exogenous ligands. These will generally be designed to complete the coordination sphere of the ion and to complement the sulfhydryl group(s) already provided by the protein. A balance must be struck between ligands that bind the ion so tightly that they weaken the sulfur/metal bond(s) to the protein thiol group(s) and reduce the stability of the radiometal label in serum, and those that provide insufficient chelating power so that the ion is easily extracted from the protein by other exogenous ligands in serum or bone marrow, or in organs such as the liver, spleen or kidneys where clearance occurs.

It must be recognized that the present approach is quite different from prior art approaches, where a multidentate ligand is first conjugated to a protein and then must be loaded with a radiometal ion to form the chelate conjugate, or where a multidentate ligand is first loaded with a radiometal ion and then conjugated to a protein. The present invention contemplates chelation of the radiometal ion with one or more thiol groups on the protein, with at least one coordination site of the ion available for binding to an exogenous ligand having superior coordinating ability to water and amine/carboxyl ligands on the protein or a transchelator added to the initial labeling solution. Only after the ions binds to one or two sulfhydryl groups is the exogenous ligand added, to fill remaining coordination sites and cap the ion.

The exogenous ligand can be monodentate or multidentate, and preferably contains at least one sulfur atom or other soft base electron pair donor group, so that it can displace weaker donor ligands in the radiometal ion coordination sphere and bind to the ion more tightly than the ligands it displaces. The function of the exogenous ligand is, in the first instance, to cap the ion and make the resultant chelate stable to further incursions which would strip the label from the protein, by enveloping the metal ion and shielding it from contact with extraneous ligands from, e.g., serum components.

Examples of such exogenous capping ligands include, e.g., monodentate sulfur/phosphorus compounds, such as simple thiols, e.g., $C_{1-30}$ mercaptoalkanes, thioesters, thioamides, thioureas, phosphines, phosphonates and the like. Bidentate ligands of the S/S, S/N, P/N and like varieties are also suitable, especially S/N ligands, e.g., mercaptopurine, 2-aminoethanethiol and the like. Tridentate S/S/N, S/N/N, and analogous phosphorus ligands, especially S/N/N ligands, can also be used. The foregoing are merely representative of the myriad types and varieties of such capping ligands that can be used to stabilize the radiometal bound to the sulfhydryl group on the protein.

Further functions can, however, be envisioned for this ligand. For example, the exogenous ligand could bear carbohydrate polymer or polyol groups to make the resultant radiometal chelate less immunogenic and to further protect it against loss of the label. Examples include any of the foregoing ligands which are linked to, e.g., dextran, polysaccharides, polyethylene glycol (PEG), and the like.

Alternatively, the exogenous ligand could bear solubilizing groups that would aid in the clearance and excretion of small metabolites of the protein, along with the radiometal. Examples include any of the foregoing ligands which also bears additional carboxyl, hydroxyl, sulfonate or like groups. Metabolism of the protein would produce short oligopeptides bearing the solubilizing groups and the latter metabolites would be more readily excreted in the urine rather than retained by the kidneys, resulting in damage to that vital organ.

A rather different function for the exogenous ligand could be to serve as a cytotoxic agent to complement and/or potentiate the radioisotope or to serve as a therapeutic agent or carrier for a therapeutic agent. One embodiment is to join a radiosensitizer to an exogenous capping ligand for use to potentiate the cytotoxic effects of a radiotherapeutic metal isotope.

Certain cytotoxic drugs are themselves candidates for use as capping ligands, e.g., 6-mercaptopurine..

The foregoing list is by no means exhaustive, and other functions, such as to enhance targeting, reduce the rate of clearance of circulating or targeted radiolabeled protein, change the biodistribution of the labeled protein or the like, can be envisioned and fall within the broad scope of the present invention.

A kit for use in radio-labeling a protein, e.g., a Fab'-SH fragment of an antibody, e.g., with Tc-99m (illustrative of the general method, with variations that would be apparent to the ordinary skilled artisan), would include, in its simplest form, the following reagents, in suitable containers, preferably sterile and under an inert gas atmosphere:

1. lyphilized, preferably stabilized, protein, e.g., Fab-SH';
2. radionuclide ions or reagents for their generation. Normally, the kit is used and/or provided incombination with one or more auxiliary reagents, buffers, filters, vials, columns and the like for effecting the radiolabeling steps.

One example of such a kit would include:

1. lyophilized Fab'-SH, stabilized with sucrose;
2. lyophilized $SnCl_2$;
3. phosphate-buffered saline (PBS), preferably containing a transchelator such as tartrate, citrate, EDTA, glucoheptonate or the like:
4. metal-free 10N HCl to dissolve the $SnCl_2$; and
5. PBS or buffer 3 to dilute the $SnCl_2$, together with sterile, argon-purged vials and syringes for effecting transfers and sterile filters for removing contaminants.

Stannous glucoheptonate is commercially available for reduction of pertechnetate and can be used in place of stannous chloride. A kit containing $F(ab')_2$ or $F(ab)_2$ together with reducing reagents, e.g., cysteine, and a column for size exclusion chromatography, can be supplied for in situ Fab'-SH or Fab-SH generation. Traut's reagent can be supplied for appending sulfhydryl groups to the protein to be labeled.

The foregoing are merely illustrative and many varients can be envisioned for use with the variations in the process of the invention described hereinabove.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

1. Preparation of Tc-99m-anti-CEA-Fab'

A solution of $SnCl_2$ is prepared by washing a piece of solid $SnCl_2$ with 1N aqueous HCl to remove surface oxide, drying and weighing, then dissolving the solid in metal-free 10N HCl, The resultant solution is diluted with metal-free distilled water and phthalate/tartrate buffer, pH 5.5 (0.13 mg Sn/ml), filtered and purged with argon.

A solution of anti-CEA-Fab'-SH is mixed with the foregoing $SnCl_2$ solution in a ratio of 13 ug Sn/mg Fab'-SH, purged with argon, and 99m-$TcO_4$ is then added (about 20 mCi/mg), at room temperature, and incubated about 30 min. The resultant labeled antibody solution contains nearly 100% of the label bound to Fab', and can be used after sterile filtration through a syringe needle equipped with a sterile filter, directly for patient injection.

2. Radioimmunodetection of lung tumor with Tc-99m-anti-CEA-Fab'

A sterile solution of Tc-99m-anti-CEA-Fab', prepared as In Example 1, is in fused intravenously into a female patient having metastatic lung cancer with involvement in both right and left lobes. As early as 1.75 hr after injection of the radio-labeled fragment, the tumors in both lungs can be detected, with improved imaging after 2–5 hr. The same patient is imaged with I-123-anti-CEA-Fab' and similar results are obtained. Negligible liver uptake of the label is seen after 2 hr and the lung involvement is readily detected, despite some blood pool activity nearby. A lesion about 1.2×2 cm in size is detectable.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for direct radio labeling of a monovalent antibody fragment, comprising the step of contacting, in solution, a mixture of (a) a monovalent Fab-SH, Fab'-SH or Fabc-SH monovalent antibody fragment produced by reductive cleavage, using a thiol reducing agent, of a divalent $F(ab)_2$ or $F(ab')_2$ precursor fragment or whole immunoglobulin, respectively, and (b) a stannous ion reducing agent for pertechnetate or perrhenate, wherein said mixture is substantially free of low molecular weight thiol compounds, with 99m-pertechnetate, 186-perrhenate or 188-perrhenate ions, and recovering the resultant solution of radiolabeled monovalent antibody fragment without purification.

2. The method of claim 1, wherein said monovalent antibody fragment in said mixture is produced by passing a solution of a monovalent Fab-SH, Fab'-SH or Fabc-SH antibody fragment, said solution also containing low molecular weight thiol compounds for reducing disulfide groups and for stabilizing sulfhydryl groups, through a sizing column to remove said low molecular weight thiol compounds, and recovering the resultant solution of monovalent Fab-SH, Fab'-SH or Fabc-SH antibody fragment which is substantially free of low molecular weight thiol compounds.

3. The method of claim 1, wherein said contacting is effected in the presence of a transchelator for reduced pertechnetate or perrhenate ions.

4. A kit suitable for radio-labeling a monovalent antibody fragment with Tc-99m, Re-186 or Re-188, comprising, in a single container, a mixture of (a) a monovalent Fab-SH, Fab'-SH Or Fabc-SH antibody fragment produced by reductive cleavage, using a thiol reducing agent, of a divalent $F(ab)_2$ or $F(ab')_2$ precursor fragment or whole immunoglobulin, respectively, and (b) a source of stannous ions for reduction of pertechnetate or perrhenate;

wherein said mixture is substantially free of low molecular weight thiol compounds.

5. The kit of claim 4, wherein said monovalent antibody fragment is Fab-SH or Fab'-SH.

6. The kit of claim 5, wherein said Fab-SH or Fab'-SH is lyophilized.

7. The kit of claim 4, wherein said source of stannous ions is stannous chloride or stannous glucoheptonate.

8. The kit of claim 4, wherein said mixture further comprises a transchelator for reduced pertechnetate or perrhenate.

9. The method of claim 1, wherein said mixture is contacted with 99m-pertechnetate ions.

10. The method of claim 1, wherein said mixture is contacted with 186-perrhenate ions.

11. The method of claim 1, wherein said mixture is contacted with 188-perrhenate ions.

12. The method of claim 9, wherein said contacting is effected in the substantial absence of oxygen.

13. The method of claim 10, wherein said contacting is effected in the substantial absence of oxygen.

14. The method of claim 11, wherein said contacting is effected in the substantial absence of oxygen.

15. The method of claim 12, wherein said contacting is effected under an argon atmosphere and all reagents are purged with argon.

16. The method of claim 13, wherein said contacting is effected under an argon atmosphere and all reagents are purged with argon.

17. The method of claim 14, wherein said contacting is effected under an argon atmosphere and all reagents are purged with argon.

18. The kit of claim 4, wherein said mixture is substantially free of oxygen.

19. The kit of claim 18, wherein all reagents are purged with argon and said mixture is maintained under an argon atmosphere.

20. A method of radio-labeling a protein consisting essentially of the steps of:
   a) incubating a protein containing disulfide bonds, selected from the group consisting of $F(ab)_2$, $F(ab')_2$ and $F(abc)_2$ immunoglobulins, with a thiol disulfide bond-reducing agent, the period of incubation being sufficient to cleave interchain heavy-heavy chain disulfide bonds to sulfhydryl groups and produce Fab, Fab' or Fabc fragments;
   b) purifying the reduced protein to substantially remove the thiol disulfide bond-reducing agent and impurities;
   c) adding $SnCl_2$ to the reduced protein in a sufficient amount to reduce a radionuclide anion selected from the group consisting of 99m-$TcO_4^-$, 186-$ReO_4^-$ and 188-$ReO_4^-$, the radionuclide to be added in a subsequent step; and
   d) radio labeling the purified reduced protein by adding said radionuclide anion, whereby the $SnCl_2$ reduces the radionuclide, and the reduced radionuclide and the sulfhydryl-containing immunoglobulin fragments form radionuclide-containing and sulfur-containing radiolabeled complexes, and wherein said method does not require conjugation to the protein of a chelator for ions of the radionuclide and does not require purification after addition of $SnCl_2$.

* * * * *